United States Patent

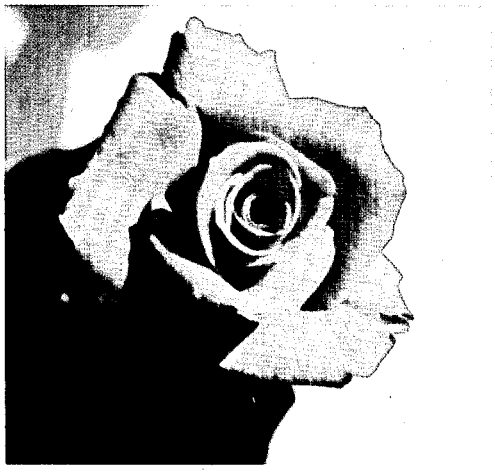
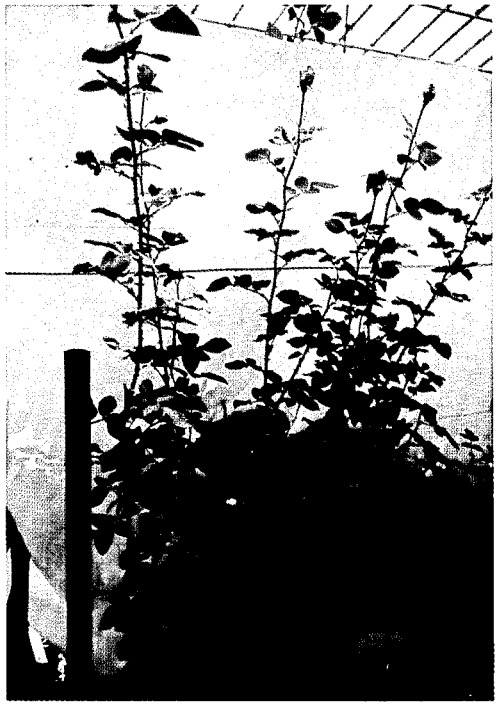

Plant Pat. 3,960

Patented Oct. 19, 1976

3,960

ROSE PLANT "T'AIME"

George Y. Umeda and Daniel S. Shinoda, San Leandro, Calif., assignors to San Lorenzo Nursery Company, San Leandro, Calif.

Filed Oct. 17, 1975, Ser. No. 623,460

Int. Cl.² A01H *5/00*

U.S. Cl. Plt.—19 1 Claim

ABSTRACT OF THE DISCLOSURE

A new variety of rose plant distinguished by its continuous production of cardinal red blooms and an exceptionally long lasting quality as cut flowers, the plant having a vigorous growth habit with the flowers being of medium size and with long stems of good strength.

BACKGROUND OF THE NEW PLANT

This new variety of rose plant originated as a seedling from a cross of "Jacqueline" (P.P. 2,183) and "Yuletide" (P.P. 1,391) made by us during breeding efforts carried on by us at San Lorenzo Nursery, at San Leandro, Calif., since May 29, 1971, in its greenhouses with the object of producing commercial cut flowers for the market of distinct red color. Asexual reproduction of this plant by buddings and potting in a propagating house in a greenhouse bed, carried on by us at San Leandro, Calif., since May 29, 1971, demonstrated that the desirable characteristics were well fixed, and propagation through successive generations by budding has shown the novel features to hold true from generation to generation.

DESCRIPTION OF THE DRAWING

Our new variety of rose plant is illustrated by the accompanying full color photographic drawing, in which:

FIG. 1 is a full face view of one of the blossoms on a stem, and

FIG. 2 is a full view of several plants in a bed in a greenhouse,

The colors shown being as nearly true as is possible to obtain by conventional photographic procedures the true color of cardinal red being shown in the color swatch appearing below the photographs.

DESCRIPTION OF THE NEW PLANT

The following is a detailed description of the garden rose plant with specifications of color according to Robert S. Wilson's Horticultural Colour Chart as issued by the British Colour Council and the The Royal Horticultural Society.

The plant

Origin: Seedling.

Parentage:

*Seed parent.*—"Jacqueline," P.P. 2,183.

*Pollen parent.*—"Yuletide," P.P. 1,391.

Classification:

*Botanic.*—Rose hybrid.

*Commercial.*—Hybrid tea.

Form: Not bushy. Grows straight upwardly.

Height: To 60 to 65 inches.

Growth: Average rate.

Habit: Tall, upright and branched.

Strength: Very good.

*Stem length.*—About 24 inches. Upper stem diameter—⅛ inch. Lower stem diameter—about ¼ inch.

Foliage: Quantity—abundant. About 12 leaves.

*Leaves.*—Shape—ovate with margin serrated. Size: 5 by 4 inches. Texture: Leathery and glossy. Color:

Upper side—Green, 139A. Lower side—Green, 139B.

*Leaflets.*—5 in number. Size: About 2½ inches. Petioles: Length—½ inch. Ribs and veins: Yes. Rachis: No. Texture: Smooth. Color: Substantially the same as full grown leaf. Thorns: Yes, at ¼ inch long. Color—Grey-Brown, 199B.

The bud

Size: Medium. About ¾ inch in diameter with a depth of 1 inch.

Form: Long, pointed and ovoid.

Opening rate: Slowly.

Sepals: Branched and pointed having a length of about 1 inch.

*Color.*—Inside — Green, 139C. Outside — Scheeles Green, 143A. When sepals first divide, the color is Oxblood Red, 183B, and when petals begin to unfurl, the color is Oxblood Red, 185A.

Calyx: Funnel shaped and broad. Does not split.

*Aspect.*—Smooth.

Peduncle: Length—2 inches. Erect and not hairy.

*Color.*—Scheeles Green, 143B.

The flower

Blooming habit: Spring, midseason and fall—profusely and continuously.

Size: Medium. 3 inches in diameter and 1½ inches in depth.

Borne: Singly.

Shape: When bloom first opens it is cup shaped, with high center, and does not change form later.

Petalage: 34 petals in loose arrangement, in cupped form, with margins ruffled.

*Color.*—Outer petals—Cardinal Red, 53C. Base, Yellow, 3C. Inside petals—Cardinal Red, 53B. Base, Yellow, 3B. Reverse side—Red, 53D.

*Texture.*—Leathery.

*Appearance.*—Velvety

Petaloids: 4 in number.

*Size.*—½ inch.

*Color.*—Cardinal Red, 53A.

Peduncle: Length—about 2 inches, sturdy and upright.

*Color.*—Scheeles Green, 143A.

Discoloration: No, after full bloom.

Effect of weather: Not affected by wet or hot weather.

Persistence: Petals do not hang on and dry.

Disease resistance: Not known.

Fragrance: Slight.

Lasting quality:

*On plant.*—10 to 12 days.

*As cut flower.*—7 to 10 days.

Reproductive organs

Stamens:

*Anthers.*—About 117, curved arrangement and about 1/16 inch long.

*Filaments.*—About ¼ inch long. Color: China Rose, 58D.

*Pollen.*—Color—Yellow-Green, 154D.

Pistils: About 106 in number.

*Styles.*—¼ inch in length.

*Stigmas.*—Color—Red-Pupple, 60C.

Characteristics of ovaries: Color—Greyed-Green, 193C.

Fruit

Fertile: Yes.

Shape: Ovoid.

Color at maturity: Yellow-Green, 152A.

This variety of rose plant is a continuous grower. Its blossom color is outstanding and distinctly different than either of its parent varieties, and does not change in storage, and with the advantageous plant habit, this new plant is outstanding as a cut commercial rose with very long, strong stems.

We claim:

1. A new and distinct variety of rose plant, substantially as herein shown and described, characterized by the cardinal red coloring of its small, high centered blossoms which are produced continuously from the spring to the fall and profusely on vigorous, upright, much branched plants which reach a height of 60 to 65 inches, the cut flowers having long lasting quality and do not change color in storage, with stems of an average length of 24 inches of excellent strength.

No references cited.

ROBERT E. BAGWILL, Primary Examiner